US008937088B2

(12) United States Patent
Wang et al.

(10) Patent No.: US 8,937,088 B2
(45) Date of Patent: Jan. 20, 2015

(54) UREAS FOR THE TREATMENT AND PREVENTION OF CANCER

(75) Inventors: Zhaoyin Wang, Kirkland (CA); Chunrong Yu, Glen Allen, VA (US)

(73) Assignees: Astar Biotech LLC, Richmond, VA (US); Beta Pharma Canada Inc., Montreal, Quebec (CA)

(*) Notice: Subject to any disclaimer, the term of this patent is extended or adjusted under 35 U.S.C. 154(b) by 0 days.

(21) Appl. No.: 13/978,693

(22) PCT Filed: Jan. 5, 2012

(86) PCT No.: PCT/US2012/020269
§ 371 (c)(1),
(2), (4) Date: Jul. 18, 2013

(87) PCT Pub. No.: WO2012/094451
PCT Pub. Date: Jul. 12, 2012

(65) Prior Publication Data
US 2013/0296380 A1    Nov. 7, 2013

Related U.S. Application Data

(60) Provisional application No. 61/457,123, filed on Jan. 6, 2011.

(51) Int. Cl.
| C07D 413/12 | (2006.01) |
| C07D 213/81 | (2006.01) |
| A61K 31/44 | (2006.01) |
| A61K 31/4439 | (2006.01) |
| A61K 45/06 | (2006.01) |

(52) U.S. Cl.
CPC ............ *C07D 213/81* (2013.01); *C07D 413/12* (2013.01); *A61K 31/44* (2013.01); *A61K 31/4439* (2013.01); *A61K 45/06* (2013.01)
USPC .......... 514/338; 514/350; 546/271.7; 546/298

(58) Field of Classification Search
None
See application file for complete search history.

(56) References Cited

U.S. PATENT DOCUMENTS

| 4,107,288 | A | 8/1978 | Oppenheim et al. |
| 5,145,684 | A | 9/1992 | Liversidge et al. |
| 5,607,915 | A | 3/1997 | Patton |
| 2005/0197370 | A1 | 9/2005 | Bossenmaier et al. |
| 2006/0189627 | A1 | 8/2006 | Laird et al. |
| 2006/0281751 | A1 | 12/2006 | Laird et al. |
| 2007/0049603 | A1 | 3/2007 | Miknis et al. |
| 2008/0045528 | A1 | 2/2008 | Sutton et al. |

FOREIGN PATENT DOCUMENTS

| EP | 1690853 A2 | 8/2006 |
| JP | 2008-513366 A2 | 5/2008 |
| JP | 2009-07871 A2 | 2/2009 |
| WO | WO 00/42012 A1 | 7/2000 |
| WO | WO 00/49001 A2 | 8/2000 |
| WO | WO 00/71536 A1 | 11/2000 |
| WO | WO0071536 A2 | 11/2000 |
| WO | WO2006059234 A2 | 6/2006 |
| WO | WO 2007/031265 A2 * | 3/2007 |
| WO | WO 2007/002325 A1 | 4/2007 |
| WO | WO 2007/002433 A1 | 4/2007 |
| WO | WO 2009/111279 A1 | 11/2009 |

OTHER PUBLICATIONS

Wu et al., Toxicology, 236, pp. 1-6, 2007.*
Rakesh K. Jain, et al., Endothelial cell death, angiogenesis, and microvascular function after castration in an androgen-dependent tumor: Role of vascular endothelial growth factor. The National Academy of Sciences, Sep. 1998, pp. 10820-10825, vol. 95.
Yoshifumi Watanabe, et al., Vascular permeability factor/vascular endothelial growth factor (VPF/VEGF) delays and induces escape from senescence in human dermal microvascular endothelial cells. Stockton Press, 1997, pp. 2025-2032.
Giorgio Bertolini, et al., A New Rational Hypothesis for the Pharmacophore of the Active Metabolite of Leflunomide, a Potent Immunosuppressive Drug. Journal Med. Chem, 1997, 40, pp. 2011-2016.
Daniel J. Hicklin, et al., Role of the Vascular Endotheilial Growth Factor Pathway in Tumor Growth and Angiogenesis. Journal of Clinical Oncology, Feb. 10, 2005, 23:pp. 1011-1027.
Laura Benjamin, et al., Selective ablation of immature blood vessels in established human tumors follows vascular endothelial growth factor withdrawal. The Journal of Clinical Investigation, Jan. 1999, vol. 103, No. 2, pp. 159-165.
Napoleone Ferrara, et al., The Biology of Vascular Endothelial Growth Factor. The Endocrine Society, Feb. 1997, vol. 18, No. 1, pp. 4-25.
Kenneth D. Bagshawe, Antibody-Directed Enzyme Prodrug Therapy: A Review. Wiley-Liss, Inc., 1995 Drug Development Research 34:220-230.
Carl-Hendrik Heldin, et al., Signal trasnduction via platelet-derived growth factor receptors. Biochimica et Biophysica Acta 1378 (1998), pp. F79-F113.
Harold F. Dvorak, et al., Vascular Permeability Factor/Vascular Endothelial Growth Factor, Microvascular Hyperpermeability, and Angiogenesis. American Journal of Pathology, May 1995, vol. 146, No. 5, pp. 1029-1039.
Hernandes, Marcelo Zaldini et al., Halogen Atoms in the Modern Medicinal Chemistry: Hints for the Drug Design, Current Drug Targets, 2010 vol. 11, No. ?, pp. 483-488.
Ramurthy, Savithri et al., Design and Synthesis of Orally Bioavailable Benzimidazoles as Raf Kinase Inhihbitors, Journal of Medicinal Chemistry 2008, 51, 7049-7052.

* cited by examiner

*Primary Examiner* — Zinna Northington Davis
(74) *Attorney, Agent, or Firm* — Weisun Rao; Greenberg Traurig, LLP

(57) ABSTRACT

A compound of Formula (I), salts thereof, prodrugs thereof, metabolites thereof, pharmaceutical compositions containing such a compound, and use of such compound and compositions to treat diseases mediated by multiple kinases, such as raf, VEGFR, PDGFR, FLT-3, and c-Kit.

21 Claims, No Drawings

UREAS FOR THE TREATMENT AND PREVENTION OF CANCER

CROSS-REFERENCE TO RELATED APPLICATIONS

This application is a U,S, national phase of PCT/US2012/020269, filed on Jan. 5 2012, which claims priority to U.S. application Ser. No, 61/457,123, filed on Jan. 6, 2011, the contents of Which are incorporated herein by reference in their entireties.

BACKGROUND OF THE INVENTION

The Raf/MEK/ERK pathway is critical for cell survival, growth, proliferation and tumorigenesis. See, e.g., Nanxin Li, et al., Current Opinion in Investigational Drugs. Vol. 8, No. 6 (2007): 452-456. Raf kinases exist as three isoforms, A-Raf, B-Raf and C-Raf. Among the three isoforms, studies have shown that B-Raf functions as the primary MEK activator. B-Raf is one of the most frequently mutated genes in human cancers. B-Raf kinase represents an excellent target for anticancer therapy based on preclinical target validation, epidemiology and drugability.

Angiogenesis, the process of blood vessel formation and growth, has been recognized as important in tumor pathophysiology and a suitable target for anti-cancer therapy VEGF is the primary mediator of both normal and tumor-associated angiogenesis through increased microvascular permeability to plasma proteins (see, e.g., D. J. Hicklin et al., *J. Clin. Oncol.* (2005) 23(5): 1011-1027), induction of endothelial cell division and migration (see, e.g., H. F. Dvorak et al., *Am. J. Pathol.*, (1995) 146(5):1029-1039, 3; N. Ferrara et al., *Endocr. Rev.* (1997) 18(1):4-25), promotion of endothelial cell survival through protection from apoptosis (see, e.g., L. E. Benjamin et al., *J. Clin. Invest.* (1999) 103(2): 159-165; R. K. Jain et al., *Proc. Natl. Acad. Sci. USA*, (1998) 95(18): 10820-10825) and reversal of endothelial cell senescence (see, e.g., Y. Watanabe et al., *Oncogene* (1997) 14(17):2025-2032). VEGF exerts its biological effect through interaction with receptors (VEGF receptors 1, 2 and 3) present on the endothelial cell surface. Upon binding of VEGF to the extracellular domain of its receptor, dimerisation and autophosphorylation of the intracellular receptor tyrosine kinase occurs and a cascade of downstream proteins are activated. Another protein relevant to tumor angiogenesis is platelet derived growth factor (PDGF). The receptor for the PDGF protein is expressed on pericytes, smooth muscle cells and capillary endothelial cells. PDGF exerts its biological effect through engagement of receptor on these vascular supporting cells, affecting processes relevant to tumour angiogenesis, including endothelial cell motility and apoptosis (see, e.g., C. H. Heldin et al., *Biochim. Biophys. Acta* (1998) 1378(1):F79-F113).

Small molecule multi-kinase inhibitors are being developed for anticancer therapy. Certain urea derivatives, which target multi-kinase including B-Raf, VRGF and PDGF, have been developed for anticancer therapy (see, e.g., WO2000042012). Inhibitors of other chemotype have also been disclosed in, e.g., US 2006/0189627, US 2006/0281751, US 2007/0049603, WO 2007/002325, WO 2007/002433, and WO2009/111279.

Pentafluorosulfanyl group is a relatively novel group in organic chemistry and it has not been found in any existing approved drugs. The present invention relates to a class of novel pentafluorosulpholane-substituted urea derivatives as multi-kinase inhibitors which targets kinases including B-Raf, VRGF and PDGF. These novel multi-kinase inhibitors also exhibit unique cycotoxicity profiles that are different from the known inhibitors. Accordingly, the compounds of the invention are useful in the treatment of hyperproliferative disorders, such as cancer. This invention also relates to pharmaceutical compositions containing a compound of the present invention and pharmaceutically acceptable salts thereof.

SUMMARY OF THE INVENTION

In one aspect, the present invention provides compounds of Formula (I) or pharmaceutically acceptable salts, prodrugs, metabolites, or isolated stereoisomers thereof.

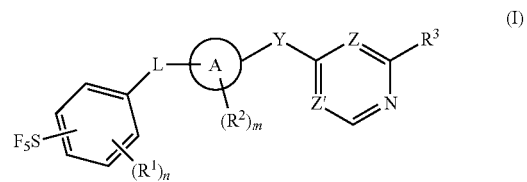

(I)

In Formula (I):
Y is O, S, S(O), S(O)$_2$, or NR$^4$;
L is —NR$^4$—X—, —X—NR$^4$—, —NR$^4$—X—NR$^4$—, —NR$^4$—, O, S;
X is —C(O)—, —C(S)—, —S(O)$_2$—, or

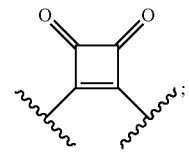 [SMILES: *c1c(*)c(=O)c1=O]

Z and Z' are each independently N or CR$^a$;
each R$^a$ is independently hydrogen, halo, C$_{1-6}$alkyl optionally substituted with one or more halo;
R$^1$ and R$^2$ are each independently alkyl, substituted alkyl, alkoxy, substituted alkoxy, amino, substituted amino, or halo;
R$^3$ is hydrogen, halo, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclyl, substituted heterocyclyl, amino, substituted amino, acyl, acylamino, alkoxy, substituted alkoxy, carboxyl, carboxyl ester, substituted C$_{1-6}$alkylsulfonyl, aminosulfonyl, or aminocarbonyl;
each R$^4$ is independently hydrogen or alkyl;
Ring A is aryl or heteroaryl; and
m and n are each independently 0, 1, 2, or 3.
In some embodiments, Y is O, S, or NR$^4$.
In some embodiments, Y is O or S.
In some embodiments, Z and Z' are each CH.
In some embodiments, R$^1$ and R$^2$ are each independently alkyl or halo.
In some embodiments, R$^1$ and R$^2$ are each independently halo (e.g., F, Cl, or Br).
In some embodiments, R$^3$ is hydrogen, halo, carboxyl, carboxyl ester, or aminocarbonyl.

In some embodiments, $R^3$ is aminocarbonyl (e.g., methylaminocarbonyl).

In some embodiments, m and n are each independently 0 or 1.

In some embodiments, the compounds of this invention are of Formula (II), and Y and W are each independently O or S.

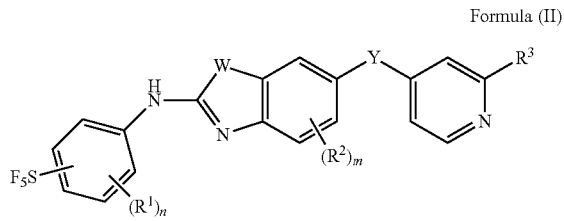

Formula (II)

In some embodiments, the compounds of this invention are of Formula (III); $R^1$ and $R^2$ are each independently halo; and $R^5$ is hydrogen or substituted alkyl.

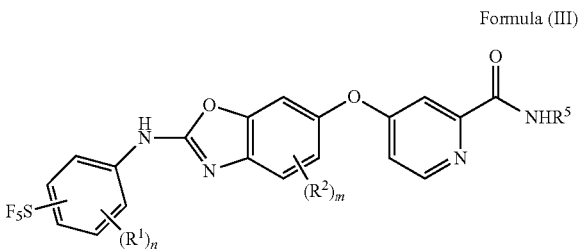

Formula (III)

In some embodiments, the compounds of this invention are of Formula (IV), and Y is O or S.

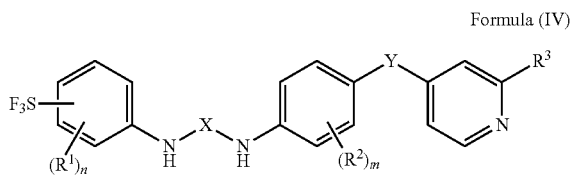

Formula (IV)

In some embodiments, the compounds of Formula (V), $R^1$ and $R^2$ are each independently hydrogen or halo, and $R^5$ is hydrogen, alkyl, or substituted alkyl.

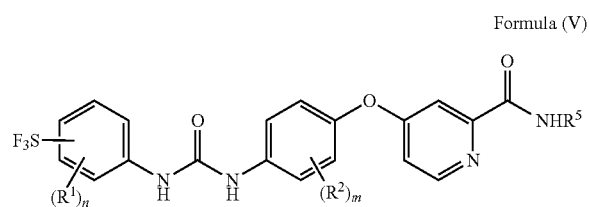

Formula (V)

In some embodiments, the compounds of this invention are:
N-Methyl-4-[4-({[3-(pentafluoro-$\lambda^6$-sulfanyl)phenyl]carbamoyl}amino)phenoxy]-pyridine-2-carboxamide;
4-[3-Fluoro-4-({[3-(pentafluoro-$\lambda^6$-sulfanyl)phenyl]carbamoyl}amino)phenoxy]-N-methylpyridine-2-carboxamide;
4-[4-({[4-Chloro-3-(pentafluoro-$\lambda^6$-sulfanyl)phenyl]carbamoyl}amino)phenoxy]-N-methylpyridine-2-carboxamide;
4-[4-({[4-Chloro-3-(pentafluoro-$\lambda^6$-sulfanyl)phenyl]carbamoyl}amino)-3-fluorophenoxy]-N-methylpyridine-2-carboxamide;
4-[4-({[2-Chloro-5-(pentafluoro-$\lambda^6$-sulfanyl)phenyl]carbamoyl}amino)phenoxy]-N-methylpyridine-2-carboxamide;
4-[4-({[2-Chloro-5-(pentafluoro-$\lambda^6$-sulfanyl)phenyl]carbamoyl}amino)-3-fluorophenoxy]-N-methylpyridine-2-carboxamide;
4-[4-({[2-Chloro-3-(pentafluoro-$\lambda^6$-sulfanyl)phenyl]carbamoyl}amino)phenoxy]-N-methylpyridine-2-carboxamide;
4-[4-({[2-Chloro-3-(pentafluoro-$\lambda^6$-sulfanyl)phenyl]carbamoyl}amino)-3-fluorophenoxy]-N-methylpyridine-2-carboxamide;
N-Methyl-4-[4-({[4-(pentafluoro-$\lambda^6$sulfanyl)phenyl]carbamoyl}amino)phenoxy]-pyridine-2-carboxamide;
4-[3-Fluoro-4-({[4-(pentafluoro-$\lambda^6$-sulfanyl)phenyl]carbamoyl}amino)phenoxy]-N-methylpyridine-2-carboxamide;
4-[4-({[4-bromo-3-(pentafluoro-$\lambda^6$-sulfanyl)phenyl]carbamoyl}amino)phenoxy]-N-methylpyridine-2-carboxamide;
4-[4-({[4-bromo-3-(pentafluoro-$\lambda^6$-sulfanyl)phenyl]carbamoyl}amino)phenoxy]-N-methylpyridine-2-carboxamide, p-toluenesulfonate;
4-[4-({[4-bromo-3-(pentafluoro-$\lambda^6$-sulfanyl)phenyl]carbamoyl}amino)-3-fluorophenoxy]-N-methylpyridine-2-carboxamide;
4-[4-({[4-bromo-3-(pentafluoro-$\lambda^6$-sulfanyl)phenyl]carbamoyl}amino)-3-fluorophenoxy]-N-methylpyridine-2-carboxamide, p-toluenesulfonate;
4-[4-({[4-chloro-3-(pentafluoro-$\lambda^6$-sulfanyl)phenyl]carbamoyl}amino)phenoxy]-N-methylpyridine-2-carboxamide, p-toluenesulfonate;
4-[4-({[4-chloro-3-(pentafluoro-$\lambda^6$-sulfanyl)phenyl]carbamoyl}amino)-3-fluorophenoxy]-N-methylpyridine-2-carboxamide, p-toluenesulfonate; and
4-[4-({[2-chloro-5-(pentafluoro-$\lambda^6$-sulfanyl)phenyl]carbamoyl}amino)phenoxy]-N-methylpyridine-2-carboxamide, p-toluenesulfonate.

In some embodiments, a compound of this inventions is a pharmaceutically acceptable salt of hydrochloric acid, hydrobromic acid, sulfuric acid, phosphoric acid, methanesulfonic acid, trifluoromethanesulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid.

Another aspect of this invention provides pharmaceutical compositions each comprising a compound of this invention and a physiologically acceptable carrier.

Yet another aspect of this invention provides methods for preventing or treating a disease in a mammal that is mediated by protein kinanse, each comprising administering to the mammal in need thereof a therapeutically effective amount of a compound of this invention. Examples of the protein kinase include VEGFR-2, PDGFR, Raf kinase, or FLT3, and c-Kit. Examples of the relevant diseases include brain cancer, lung cancer, kidney cancer, bone cancer, liver cancer, bladder cancer, breast cancer, head and neck cancer, esophageal cancer, stomach cancer, colon cancer, rectum cancer, breast cancer, ovarian cancer, melanoma, skin cancer, adrenal cancer, cervical cancer, lymphoma, pancreatic cancer, or thyroid tumor, or any of their complications. Unexpectedly, the compounds of this invention, with the pentafluorosulfanyl substitient on a phenyl group (which is a major difference from the comparables Sorefenib® or Regorafenib®) possess at least comparable but generally better effect in inhibiting kinases that are involved in numerous diseases such as cancer, and therefore more effective in treating such diseases.

In some embodiments, the methods each further include administering to the mammal an additional anti-cancer agent. Examples of the additional anti-cancer agent include an aromatase inhibitor, an antiestrogen, an anti-androgen (especially in the case of prostate cancer) or a gonadorelin agonist, a topoisomerase I inhibitor or a topoisomerase II inhibitor, a microtubule active agent, an alkylating agent, an antineoplastic antimetabolite or a platin compound, a compound targeting/decreasing a protein or lipid kinase activity or a protein or lipid phosphatase activity, a further anti-angiogenic compound or a compound which induces cell differentiation processes, a bradykinin I receptor or an angiotensin II antagonist, a cyclooxygenase inhibitor, a bisphosphonate, a rapamycin derivative such as everolimus (mTOR inhibitors), a heparanase inhibitor (prevents heparan sulphate degradation), e.g., Pl 88, a biological response modifier, preferably a lymphokine or interferons, e.g. interferon if, an ubiquitination inhibitor, or an inhibitor which blocks anti-apoptotic pathways (e.g., obatoclax or navitoclax), an inhibitor of Ras oncogenic isoforms, e. g. H-Ras, K-Ras or N-Ras, or a farnesyl transferase inhibitor, e.g. L-744, 832 or DK8G557, a telomerase inhibitor, e.g. telomestatin, a protease inhibitor, a matrix metalloproteinase inhibitor, a methionine aminopeptidase inhibitor, e.g. bengamide or a derivative thereof, or a proteosome inhibitor, a histone deacetylase inhibitor, inhibitors of the PKB pathway, inhibitors of the Raf/MEK ERK pathway. Further examples of the additional anti-cancer agent include asparaginase, bleomycin, carboplatin, carmustine, chlorambucil, cisplatin, colaspase, cyclophosphamide, cytarabine, dacarbazine, dactinomycin, daunorabicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, vindesine, amino glut ethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine, oxaliplatin, gemcitabine, capecitabine, epothilone, tositumomab, trabedectin, and temozolomide. trastuzumab, cetuximab, bevacizumab, pertuzumab, Iressa, Tarceva, icotinib, crizotinib, NVP-TAE684, canertinib, lapatinib, CP-724,714, masitinib, neratinib, pelitinib, Gleevec, vatalanib, sunitinib, vandetanib, axitinib, CP-547,632, CP-673,451, Vemurafenib, dovitinib, tandutinib, cediranib, PD-325901, selumetinib, suberoylanilide hydroxamic acid (SAHA), LAQ-824, panobinostat, entinostat, romidepsin, bortezomib, and temsirolimus.

Also within the scope of this invention is the use of one ore more compounds of this invention for manufacturing a medicament for the treatment or prevention of a disease mediated by one or more protein kinase as described above. Examples of such diseases are also provided above. Optionally, a medicament thus manufactured can contain one or more anticancer agents as described and exemplified above.

DETAILED DESCRIPTION OF THE INVENTION

Throughout this application, the text refers to various embodiments of the present compounds, compositions, and methods. The various embodiments described are meant to provide variety illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

As used herein, the term "alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl [i.e., $CH_3$—], ethyl [i.e., $CH_3CH_2$—], n-propyl [i.e., $CH_3CH_2CH_2$—], isopropyl [i.e., $(CH_3)_2CH$—], n-butyl [i.e., $CH_3CH_2CH_2CH_2$—], isobutyl [i.e., $(CH_3)_2CHCH_2$—], sec-butyl [i.e., $(CH_3)(CH_3CH_2)CH$—], t-butyl [i.e., $(CH_3)_3C$—], n-pentyl [i.e., $CH_3CH_2CH_2CH_2CH_2$—], and neopentyl [i.e., $(CH_3)_3CCH_2$—].

As used herein, the term "substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, spirocycloalkylidene, $SO_3H$, substituted sulfonyl, sulfonyloxy, thioacyl, thiocyanate, thiol, alkylthio, and substituted alkylthio, wherein said substituents are defined herein.

As used herein, the term "alkylidene" or "alkylene" refers to divalent saturated aliphatic hydrocarbyl groups having from 1 to 10 carbon atoms and preferably 1 to 6 carbon atoms. The alkylidene and alkylene groups include branched and straight chain hydrocarbyl groups.

As used herein, the term "substituted alkylidene" or "substituted alkylene" refers to an alkylidene group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, oxo, thione, spirocycloalkylidene, SO₃H, substituted sulfonyl, sulfonyloxy, thioacyl, thiocyanate, thiol, alkylthio, and substituted alkylthio, wherein said substituents are defined herein.

As used herein, the term "alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

As used herein, the term "substituted alkoxy" refers to the group —O-(substituted alkyl) wherein substituted alkyl is defined herein.

As used herein, the term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, substituted hydrazino-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, substituted hydrazino, heteroaryl, substituted heteroaryl, heterocyclic and substituted heterocyclic are as defined herein. Acyl includes the "acetyl" group CH₃C(O)—.

As used herein, the term "acylamino" refers to the groups —NRC(O)alkyl, —NRC(O)substituted alkyl, —NRC(O)cycloalkyl, —NRC(O)substituted cycloalkyl, —NRC(O)cycloalkenyl, —NRC(O)substituted cycloalkenyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

As used herein, the term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

As used herein, the term "amino" refers to the group —NH₂.

As used herein, the term "substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —SO₂-alkyl, —SO₂-substituted alkyl, —SO₂-alkenyl, —SO₂-substituted alkenyl, —SO₂-cycloalkyl, —SO₂-substituted cylcoalkyl, —SO₂-cycloalkenyl, —SO₂-substituted cylcoalkenyl, —SO₂-aryl, —SO₂-substituted aryl, —SO₂-heteroaryl, —SO₂-substituted heteroaryl, —SO₂-heterocyclic, and —SO₂-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

As used herein, the term "hydroxyamino" refers to the group —NHOH.

As used herein, the term "alkoxyamino" refers to the group —NHO-alkyl wherein alkyl is defined herein.

As used herein, the term "amino carbonyl" refers to the group —C(O)NR'R" where R' and R" are independently selected from the group consisting of hydrogen, alk4yl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, substituted heterocyclyl, hydroxy, alkoxy, substituted alkoxy, amino, substituted amino, and acylamino, and where R" and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

As used herein, the term "aminothiocarbonyl" refers to the group —C(S)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R' and R' are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

As used herein, the term "aminocarbonylamino" refers to the group —NRC(O)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

As used herein, the term "aminothiocarbonylamino" refers to the group —NRC(S)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

As used herein, the term "aminocarbonyloxy" refers to the group —OC(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

As used herein, the term "aminosulfonyl" refers to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

As used herein, the term "aminosulfonyloxy" refers to the group —OSO$_2$NR'R" where R' and R' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

As used herein, the term "aminosulfonylamino" refers to the group —NR—SO$_2$NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

As used herein, the term "amidino" refers to the group —C(=NR)NR'R" where R, R', and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

As used herein, the term "aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

As used herein, the term "substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, amino sulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, —SF$_5$, substituted heterocyclylthio, nitro, SO$_3$H, substituted sulfonyl, sulfonyloxy, thioacyl, thiocyanate, thiol, alkylthio, and substituted alkylthio, wherein said substituents are defined herein.

As used herein, the term "aryloxy" refers to the group —O-aryl, where aryl is as defined herein, that includes, by way of example, phenoxy and naphthoxy.

As used herein, the term "substituted aryloxy" refers to the group —O-(substituted aryl) where substituted aryl is as defined herein.

As used herein, the term "arylthio" refers to the group —S-aryl, where aryl is as defined herein.

As used herein, the term "substituted arylthio" refers to the group —S-(substituted aryl), where substituted aryl is as defined herein.

As used herein, the term "alkenyl" refers to alkenyl groups having from 2 to 6 (e.g, from 2 to 4) carbon atoms and having at least 1 (e.g., from 1 to 2) site of vinyl unsaturation (>C=C<). Such groups are exemplified by vinyl, allyl, and but-3-en-yl.

As used herein, the term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, amino sulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyoxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

As used herein, the term "alkynyl" refers to hydrocarbyl groups having from 2 to 6 carbon atoms and preferably 2 to 3 carbon atoms and having at least 1 and preferably from 1 to 2 sites of acetylenic unsaturation (—C≡C—).

As used herein, the term "substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyoxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to an acetylenic carbon atom.

As used herein, the term "azido" refers to the group —$N_3$.

As used herein, the term "hydrazino" refers to the group —$NHNH_2$.

As used herein, the term "substituted hydrazino" refers to the group —NRNR'R" where R, R', and R" are independently selected from the group consisting of hydrogen, alkyl, substituted alkyl, alkenyl, substituted alkenyl, alkynyl, substituted alkynyl, aryl, substituted aryl, carboxyl ester, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

As used herein, the term "cyano" or "carbonitrile" refers to the group —CN.

As used herein, the term "cyanate" refers to the group —OCN.

As used herein, the term "carbonyl" refers to the divalent group —C(O)-which is equivalent to —C(=O)—.

As used herein, the term "carboxyl" or "carboxy" refers to —COOH or salts thereof.

As used herein, the term "carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

As used herein, the term "(carboxyl ester)amino" refers to the group —NR—C(O)O-alkyl, —NR—C(O)O-substituted alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

As used herein, the term "(carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

As used herein, the term "cycloalkyl" refers to cyclic alkyl groups of from 3 to 10 carbon atoms having single or multiple cyclic rings including fused, bridged, and spiro ring systems. In fused ring systems, one or more the rings can be cycloalkyl, heterocyclic, aryl, or heteroaryl provided that the point of attachment is through the cycloalkyl ring. Examples of suitable cycloalkyl groups include, for instance, adamantyl, cyclopropyl, cyclobutyl, cyclopentyl, and cyclooctyl.

As used herein, the term "cycloalkenyl" refers to non-aromatic cyclic alkyl groups of from 4 to 10 carbon atoms having single or multiple cyclic rings and having at least one >C=C< ring unsaturation and preferably from 1 to 2 sites of >C=C< ring unsaturation.

As used herein, the term "substituted cycloalkyl" and "substituted cycloalkenyl" respectively refer to a cycloalkyl group and a cycloalkenyl group each having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are defined herein.

As used herein, the term "cycloalkyloxy" refers to —O-cycloalkyl.

As used herein, the term "substituted cycloalkyloxy refers to —O-(substituted cycloalkyl).

As used herein, the term "cycloalkylthio" refers to —S-cycloalkyl.

As used herein, the term "substituted cycloalkylthio" refers to —S-(substituted cycloalkyl).

As used herein, the term "cycloalkenyloxy" refers to —O-cycloalkenyl.

As used herein, the term "substituted cycloalkenyloxy" refers to —O-(substituted cycloalkenyl).

As used herein, the term "cycloalkenylthio" refers to —S-cycloalkenyl.

As used herein, the term "substituted cycloalkenylthio" refers to —S-(substituted cycloalkenyl). "Guanidino" refers to the group —NHC(=NH)NH_2.

As used herein, the term "substituted guanidino" refers to —NRC(=NR)N(R)_2 where each R is independently selected from the group consisting of hydrogen, alkyl, substituted alkyl, aryl, substituted aryl, heteroaryl, substituted heteroaryl, heterocyclyl, and substituted heterocyclyl and two R groups attached to a common guanidino nitrogen atom are optionally joined together with the nitrogen bound thereto to form a heterocyclic or substituted heterocyclic group, provided that at least one R is not hydrogen, and wherein said substituents are as defined herein.

As used herein, the term "halo" or "halogen" refers to fluoro, chloro, bromo and iodo.

As used herein, the term "halo alkyl" refers to substitution of alkyl groups with 1 to 5 or preferably 1 to 3 halo groups.

As used herein, the term "haloalkoxy" refers to substitution of alkoxy groups with 1 to 5 or preferably 1 to 3 halo groups.

As used herein, the term "hydroxy" or "hydroxyl" refers to the group —OH.

As used herein, the term "heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings mayor may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N~O), sulfinyl, or sulfonyl moieties. Preferred heteroaryls include pyridinyl, pyrrolyl, indolyl, thiophenyl, and furanyl.

As used herein, the term "substituted heteroaryl" refers to heteroaryl groups that are substituted with from 1 to 5, preferably 1 to 3, or more preferably 1 to 2 substituents selected from the group consisting of the same group of substituents defined for substituted aryl.

As used herein, the term "heteroaryloxy" refers to —O-heteroaryl.

As used herein, the term "substituted heteroaryloxy refers to the group —O-(substituted heteroaryl).

As used herein, the term "heteroarylthio" refers to the group —S-heteroaryl.

As used herein, the term "substituted heteroarylthio" refers to the group —S-(substituted heteroaryl).

As used herein, the term "heterocycle" or "heterocyclic" or "heterocycloalkyl" or "heterocyclyl" refers to a saturated, partially saturated, or unsaturated group (but not aromatic) having a single ring or multiple condensed rings, including fused bridged and spirocyclyl ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, and sulfonyl moieties.

As used herein, the term "substituted heterocyclic" or "substituted heterocycloalkyl" or "substituted heterocyclyl" refers to heterocyclyl groups that are substituted with from 1 to 5 (e.g., from 1 to 3) of the same substituents as defined for substituted cycloalkyl.

As used herein, the term "heterocyclyloxy" refers to the group —O-heterocyclyl.

As used herein, the term "substituted heterocyclyloxy" refers to the group —O-(substituted heterocyclyl).

As used herein, the term "heterocyclylthio" refers to the group —S-heterocyclyl.

As used herein, the term "substituted heterocyclylthio" refers to the group —S-(substituted heterocyclyl). Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

As used herein, the term "nitro" refers to the group —NO$_2$.

As used herein, the term "oxo" refers to the atom (=O).

As used herein, the term "oxide" refers to products resulting from the oxidation of one or more heteroatoms. Examples include N-oxides, sulfoxides, and sulfones.

As used herein, the term "spirocyclyl" refers to divalent cyclic groups from 3 to 10 carbon atoms having a cycloalkyl or heterocyclyl ring with a spiro union (the union formed by a single atom which is the only common member of the rings) as exemplified by the following structure:

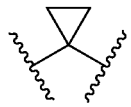 [SMILES: *C1(*)CC1]

As used herein, the term "spirocycloalkyl" or "spirocycloalkylidene" refers to divalent cyclic groups having a cycloalkyl ring with a spiro union, as described for spirocyclyl.

As used herein, the term "sulfonyl" refers to the divalent group —SO$_2$—.

As used herein, the term "substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

As used herein, the term "sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

As used herein, the term "thioacyl" refers to the groups R—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

As used herein, the term "thiol" refers to the group —SH.

As used herein, the term "alkylthio" refers to the group —S-alkyl wherein alkyl is as defined herein.

As used herein, the term "substituted alkylthio" refers to the group —S-(substituted alkyl) wherein substituted alkyl is as defined herein.

As used herein, the term "thiocarbonyl" refers to the divalent group —C(S)-which is equivalent to —C(=S)—.

As used herein, the term "thione" refers to the atom (=S).

As used herein, the term "thiocyanate" refers to the group —SCN.

As used herein, the term "solvate" or "solvates" refer compounds or a salt thereof that are bound to a stoichiometric or non-stoichiometric amount of a solvent. Preferred solvents are volatile, non-toxic, and/or acceptable for administration to humans in trace amounts. Suitable solvates include water.

As used herein, the term "stereoisomer" or "stereoisomers" refer to compounds that differ in the chirality of one or more stereocenters. Stereoisomers include enantiomers and diastereomers.

As used herein, the term "tautomer" refer to alternate forms of a compound that differ in the position of a proton, such as enol-keto and imine-enamine tautomers, or the tautomeric forms of heteroaryl groups containing a ring atom attached to both a ring —NH-moiety and a ring =N-moiety such as pyrazoles, imidazoles, benzimidazoles, triazoles, and tetrazoles.

"Prodrug" refers to any derivative of a compound of the embodiments that is capable of directly or indirectly providing a compound o of the embodiments or an active metabolite or residue thereof when administered to a subject. Particularly favoured derivatives and prodrugs are those that increase the bioavailability of the compounds of the embodiments when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester forms of the compounds of the invention. Examples of ester prodrugs include formate, acetate, propionate, butyrate, acrylate, and ethylsuccinate derivatives. A general overview of prodrugs is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein, the term "pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate. The term also includes pharmaceutically acceptable salts of stereo isomers, tautomers, esters, and prodrugs of the compound.

One embodiment is directed to compounds, stereoisomers, tautomers, solvates, oxides, esters, and prodrugs of Formula (I), Formula (II), Formula (III), Formula (IV), and Formula (V), the pharmaceutically acceptable salts thereof, and the related compositions and methods.

The compounds of this invention, including those of Formula (I), Formula (II), Formula (III), Formula (IV), and Formula (V) or salts thereof may be formulated into compositions. In a preferred embodiment, the composition is a pharmaceutical composition.

Another aspect of this invention relates to a method of treating or preventing diseases with a therapeutically effective amount of a compound of Formula (I), Formula (II), Formula (III), Formula (IV), and Formula (V) or a pharmaceutical composition thereof. Such diseases include, without limitation, colon, breast, stomach, ovarian cancer or other cell proliferative disorders.

As used herein, the term "cell proliferative disorder" refers to conditions in which unregulated or abnormal growth, or both, of cells can lead to the development of an unwanted condition or disease, which may or may not be cancerous. In one aspect, a cell proliferative disorder includes a non-cancerous condition, e.g., rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus. In another aspect, a cell proliferative disorder includes a precancer or a precancerous condition. In another aspect, a cell proliferative disorder includes cancer. Various cancers to be treated include but are not limited to breast cancer, lung cancer, colorectal cancer, pancreatic cancer, ovarian cancer, prostate cancer, renal carcinoma, hepatoma, brain cancer, melanoma, multiple myeloma, chronic myelogenous leukemia, hematologic tumor, and lymphoid tumor, including metastatic lesions in other tissues or organs distant from the primary tumor site. Cancers to be treated include but are not limited to sarcoma, carcinoma, and adenocarcinoma. In one aspect, a "precancer cell" or "precancerous cell" is a cell manifesting a cell proliferative disorder that is a precancer or a precancerous condition. In another aspect, a "cancer cell" or "cancerous cell" is a cell manifesting a cell proliferative disorder that is a cancer. Any reproducible means of measurement may be used to identify cancer cells or precancerous cells. In a preferred aspect, cancer cells or precancerous cells are identified by histological typing or grading of a tissue sample (e.g., a biopsy sample). In another aspect, cancer cells or precancerous cells are identified through the use of appropriate molecular markers.

While the compounds of the preferred embodiments can be administered as the sole active pharmaceutical agent, they can also be used in combination with one or more other agents used in the treatment of cancer. The compounds of the preferred embodiments are also useful in combination with known therapeutic agents and anti-cancer agents, and combinations of the presently disclosed compounds with other anti-cancer or chemotherapeutic agents are within the scope of the preferred embodiments. Examples of such agents can be found in Cancer Principles and Practice of Oncology, V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signalling, apoptosis inducing agents and agents that interfere with cell cycle checkpoints. The compounds of the preferred embodiments are also useful when co-administered with radiation therapy.

Therefore, in one embodiment, the compounds are also used in combination with known anticancer agents including, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

In general, the compounds of preferred embodiments will be administered in a therapeutically effective amount by any of the accepted modes of administration for agents that serve similar utilities. The actual amount of the compound of preferred embodiments, i.e., the active ingredient, will depend upon numerous factors such as the severity of the disease to be treated, the age and relative health of the subject, the potency of the compound used the route and form of administration, and other factors. The drug can be administered more than once a day, preferably once or twice a day. All of these factors are within the skill of the attending clinician.

Effective amounts of the compounds of the preferred embodiments generally include any amount sufficient to effectively treat the diseases or alleviation symptoms of the disease such as cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the preferred embodiments, a therapeutically effective dose generally can be a total daily dose administered to a host in single or divided doses may be in amounts, for example, of from about 0.001 to about 1000 mg/kg body weight daily and more preferred from about 1.0 to about 30 mg/kg body weight daily. Dosage unit compositions may contain such amounts of submultiples thereof to make up the daily dose.

The choice of formulation depends on various factors such as the mode of drug administration and bioavailability of the drug substance. In general, compounds of preferred embodiments can be administered as pharmaceutical compositions by anyone of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of preferred embodiments is inhalation. This is an effective method for delivering a therapeutic agent directly to the respiratory tract (see, e.g., U.S. Pat. No. 5,607,915).

Suitable pharmaceutically acceptable carriers or excipients include, e.g., processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-B-cyclodextrin, polyvinylpyrrolidinone, low melting waxes, ion exchange resins, and the like, as well as combinations of any two or more thereof. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutically acceptable excipients are described in "Remington's Pharmaceutical Sciences," Mack Pub. Co., New Jersey (1991), incorporated herein by reference.

As used herein, the term "pharmaceutically acceptable salts" refers to the nontoxic acid or alkaline earth metal salts of the compounds of Formulae (I), (II), (III), (IV), or (V). These salts can be prepared in situ during the final isolation and purification of the compounds of Formulae (I), (II), (III), (IV), or (V), or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with agents such as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methane sulfonic acid, succinic acid and citric acid. Basic addition salts can be prepared in situ during the final isolation and purification of the compounds of Formulae (I), (II), (III), (IV), or (V), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethyl amine, trimethylamine, triethylamine, ethyl amine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the preferred embodiments which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the embodiments. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

It will be apparent to those skilled in the art that the compounds of the preferred embodiments, including the compounds of Formulae (I), (II), (III), (IV), or (V) or their tautomers, pro drugs, and stereoisomers, as well as the pharmaceutically acceptable salts, esters and prodrugs of any of them, may be processed in vivo through metabolism in a human or animal body or cell to produce metabolites. The term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. The metabolites of a compound of the embodiments may be identified using routine techniques known in the art. See, e.g., G. Bertolini et al., *J Med. Chem.* (1997) 40:2011-2016; D. Shan et al., *J Pharm. Sci.* (1997) 86(7):765-767; K. Bagshawe, *Drug Dev. Res.* (1995) 34:220-230; N. Bodor, *Advances in Drug Res.* (1984) 13:224-331; H. Bundgaard, *Design of Prodrugs* (Elsevier Press 1985); and I. K. Larsen, Design and Application of Prodrugs, *Drug Design and Development* (Krogsgaard-Larsen et al., eds., Harwood Academic Publishers, 1991). It should be understood that individual chemical compounds that are metabolites of the compounds of Formulae (I), (II), (III), (IV), or (V) or their tautomers, prodrugs, and stereoisomers, as well as the pharmaceutically acceptable salts, esters and prodrugs of any of them, are included within the preferred embodiments.

The compounds of the preferred embodiments may be administered orally, parenterally, sub lingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intrathecal, intramuscular, intrastemal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluents or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with suitable non-irritating excipients such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavouring, and perfuming agents.

The compounds of the preferred embodiments can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the preferred embodiments, stabilizers, preservatives, excipients, and the like. The preferred lipids are the phospholipids and phosphatidyl cholines (lecithins), both natural and synthetic. Methods to form liposomes are known in the art. See, e.g., Prescott, ed., Methods in Cell Biology, Volume XIV, Academic Press, New York, N.W., p. 33 et seq. (1976).

Compressed gases may be used to disperse a compound of preferred embodiments in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, $18^{th}$ ed., 1990).

For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from about 10 to about 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of about 400 nm) in the presence of a surface modifier and then dispersed in a liquid medium to give a pharmaceutical formulation that exhibits remarkably high bioavailability.

PREPARATION OF COMPOUNDS OF THIS INVENTION

Schemes 1-2 illustrate general methods for the preparation of intermediates and compounds of the embodiments. These compounds are prepared from starting materials either known in the art or are commercially available. The specific compounds are for illustrative purposes only.

Scheme 1

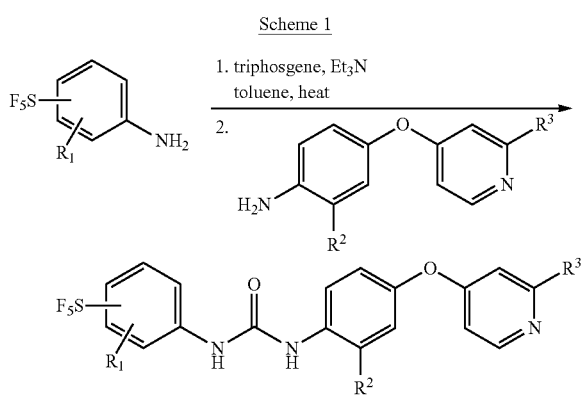

In Scheme 1, the SF$_5$-substituted aniline can be transformed to its isocyanate intermediate by treatment with triphosgene and a base. The isocyanate intermediate can react with appropriate aniline to form the urea product.

Scheme 2

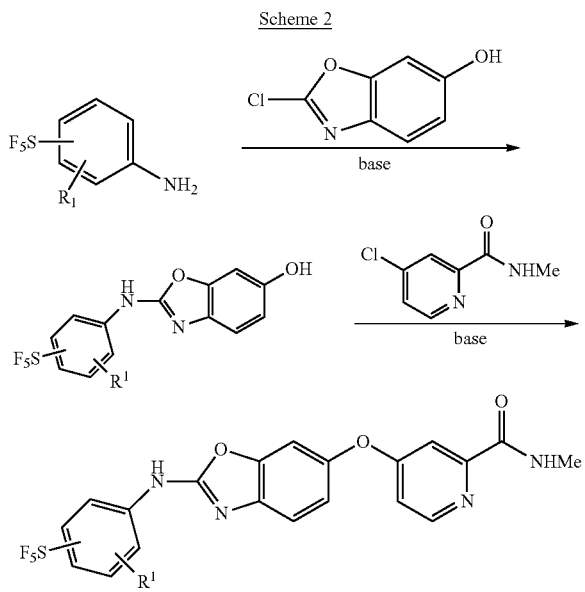

In Scheme 2, the coupling of the SF$_5$-substituted aniline with a chlorobenzoxazole can be achieved by treatment with a base. The intermediate can be further coupled with a chloropyridine in the presence of a base to provide the compound of the invention.

Referring to the examples that follow, exemplary compounds of this invention have been synthesized using the methods described herein, or other methods, which are known in the art. It is understood that the invention is not limited to the embodiments set forth herein for illustration, but embraces all such forms thereof as come within the scope of the above disclosure.

Example 1

N-methyl-4-[4-({[3-(pentafluoro-λ$^6$-sulfanyl)phenyl]carbamoyl}amino)phenoxy]pyridine-2-carboxamide To a solution of 3-(pentafluoro-λ$^6$-sulfanyl)aniline (0.9 g, 4 mmol) in 70 mL of dry toluene was treated with 0.81 g of triphosgene, and immediately followed by 0.66 ml of Et$_3$N. The cloudy suspension was heated at 70° C. for 1 h and cooled to room temperature. The reaction mixture was then diluted with 40 mL of hexane, filtered, and concentrated to give the crude isocyanate. The crude isocyanate was dissolved in 40 mL of Cl$_2$CH$_2$CH$_2$Cl$_2$/toluene (1:1) and treated with 0.85 g of 4-(4-aminophenoxy)-N-methylpicolinamide. The reaction mixture was stirred overnight and concentrated. The crude product was purified by silica gel chromatography eluted with a gradient up to 80% EtOAc/Hexane to give the desired product (1.3 g).

$^1$H NMR (400 MHz, DMSO-d$_6$): δ 9.20 (s, 1H), 8.98 (s, 1H), 8.78 (m, 1H), 8.53 (d, 1H), 8.26 (s, 1H), 7.45-7.62 (m, 5H), 7.40 (d, 1H), 7.13-7.20 (m, 3H), 2.80 (d, 3H).

Example 2

4-[3-fluoro-4-({[3-(pentafluoro-λ$^6$-sulfanyl)phenyl]carbamoyl}amino)phenoxy]-N-methylpyridine-2-carboxamide Following the same procedure described in Example 1, the title compound was prepared from 3-(pentafluoro-λ$^6$-sulfanyl)aniline aniline and 4-(4-amino-3-fluorophenoxy)-N-methylpyridine-2-carboxamide as a white solid.

$^1$H NMR (400 MHz, DMSO-d$_6$): δ 9.51 (s, 1H), 8.82 (m, 1H), 8.73 (s, 1H), 8.53 (d, 1H), 8.28 (s, 1H), 8.18 (t, 1H), 7.49-7.58 (m, 3H), 7.42 (d, 1H), 7.35 (dd, 1H), 7.19 (dd, 1H), 7.08 (d, 1H), 2.80 (d, 3H).

Example 3

4-[4-({[4-chloro-3-(pentafluoro-λ$^6$-sulfanyl)phenyl]carbamoyl}amino)phenoxy]-N-methylpyridine-2-carboxamide Step 1. 4-chloro-3-(pentafluoro-λ$^6$-sulfanyl)aniline NCS (7.94 g, 59.4 mmol) was added to a solution of 3-pentafluoroaniline (10.02 g, 45.7 mmol) in anhydrous dichloroethane (229 mL) under nitrogen at room temperature. After stirring at 50° C. overnight, the reaction mixture was cooled to room temperature and 200 mL of a cold saturated solution of Na$_2$SO$_3$ and 100 mL of an half saturated solution of NaHCO$_3$ were added sequentially. Two layers were separated and the aqueous layer was extracted with dichloromethane (2×100 mL). The combined organic layers were washed with brine (100 mL), dried over Na$_2$SO$_4$ and then filtered. The filtrate was concentrated and the residue was purified by flash column chromatography eluted with gradient of 10% to 20% of EtOAc in hexanes to give the products in the following order:

2-chloro-5-(pentafluoro-λ$^6$-sulfanyl)aniline, 4.5 g.
$^1$H NMR (400 MHz, DMSO-d$_6$): δ 7.40 (d, 1H), 7.30 (d, 1H), 6.98 (dd, 1H), 5.92 (s, 2H).

2-chloro-3-(pentafluoro-λ$^6$-sulfanyl)aniline, 3.6 g
$^1$H NMR (400 MHz, DMSO-d$_6$): δ 7.22 (dd, 1H), 7.16 (d, 1H), 7.05 (d, 1H), 5.98 (s, 2H).

4-chloro-3-(pentafluoro-λ$^6$-sulfanyl)aniline, 2.0 g.
$^1$H NMR (400 MHz, DMSO-d$_6$): δ 7.29 (d, 1H), 7.19 (d, 1H), 6.77 (dd, 1H), 5.83 (s, 2H).

Step 2. 4-[3-fluoro-4-({[3-(pentafluoro-λ$^6$-sulfanyl)phenyl]carbamoyl}amino)phenoxy]-N-methylpyridine-2-carboxamide Following the same procedure described in Example 1, the title compound was prepared from 4-chloro-3-(pentafluoro-λ$^6$-sulfanyl)aniline and 4-(4-aminophenoxy)-N-methylpicolinamide as a beige solid.

¹H NMR (400 MHz, DMSO-d$_6$): δ 9.30 (s, 1H), 9.03 (s, 1H), 8.78 (m, 1H), 8.51 (s, 1H), 8.41 (d, 1H), 7.55-7.68 (m, 4H), 7.38 (d, 1H), 7.18 (d, 2H), 7.15 (dd, 1H), 2.80 (d, 3H).

Example 4

4-[4-({[4-chloro-3-(pentafluoro-λ$^6$-sulfanyl)phenyl]carbamoyl}amino)-3-fluorophenoxy]-N-methylpyridine-2-carboxamide Following the same procedure described in Example 1, the title compound was prepared from 4-chloro-3-(pentafluoro-λ$^6$-sulfanyl)aniline and 4-(4-amino-3-fluorophenoxy)-N-methylpyridine-2-carboxamide as a white solid.

¹H NMR (400 MHz, DMSO-d$_6$): δ 9.61 (s, 1H), 8.70 (m, 1H), 8.75 (s, 1H), 8.53 (d, 1H), 8.42 (d, 1H), 8.13 (t, 1H), 7.67 (d, 1H), 7.57 (dd, 1H), 7.42 (d, 1H), 7.35 (dd, 1H), 7.20 (m, 1H), 7.08 (d, 1H), 2.80 (d, 3H).

Example 5

4-[4-({[2-chloro-5-(pentafluoro-λ$^6$-sulfanyl)phenyl]carbamoyl}amino)phenoxy]-N-methylpyridine-2-carboxamide Following the same procedure described in Example 1, the title compound was prepared from 2-chloro-5-(pentafluoro-λ$^6$-sulfanyl)aniline and 4-(4-aminophenoxy)-N-methylpicolinamide as a beige solid.

¹H NMR (400 MHz, DMSO-d$_6$): δ 9.72 (s, 1H), 8.78 (s, 1H), 8.77 (m, 1H), 8.70 (s, 1H), 8.52 (d, 1H), 7.75 (d, 1H), 7.62 (d, 2H), 7.55 (dd, 1H), 7.49 (s, 1H), 7.20 (d, 2H), 7.15 (dd, 1H), 2.80 (d, 3H).

Example 6

4-[4-({[2-chloro-5-(pentafluoro-λ$^6$-sulfanyl)phenyl]carbamoyl}amino)-3-fluorophenoxy]-N-methylpyridine-2-carboxamide Following the same procedure described in Example 1, the title compound was prepared from 2-chloro-5-(pentafluoro-λ$^6$-sulfanyl)aniline and 4-(4-amino-3-fluorophenoxy)-N-methylpyridine-2-carboxamide as a beige solid.

¹H NMR (400 MHz, DMSO-d$_6$): δ 9.62 (s, 1H), 9.14 (s, 1H), 8.85 (d, 1H), 8.80 (m, 1H), 8.53 (d, 1H), 8.25 (t, 1H), 7.74 (d, 1H), 7.58 (dd, 1H), 7.42 (d, 1H), 7.36 (dd, 1H), 7.20 (dd, 1H), 7.08 (d, 1H), 2.80 (d, 3H).

Example 7

4-[4-({[2-chloro-3-(pentafluoro-λ$^6$-sulfanyl)phenyl]carbamoyl}amino)phenoxy]-N-methylpyridine-2-carboxamide Following the same procedure described in Example 1, the title compound was prepared from 2-chloro-3-(pentafluoro-λ$^6$-sulfanyl)aniline and 4-(4-aminophenoxy)-N-methylpicolinamide as a white solid.

¹H NMR (400 MHz, DMSO-d$_6$): δ 9.65 (s, 1H), 8.78 (m, 1H), 8.68 (s, 1H), 8.52 (d, 1H), 8.40 (d, 1H), 7.80 (d, 1H), 7.62 (d, 2H), 7.53-7.50 (m, 1H), 7.48 (dd, 1H), 7.20 (d, 2H), 7.15 (dd, 1H), 2.78 (d, 3H).

Example 8

4-[4-({[2-chloro-3-(pentafluoro-λ$^6$-sulfanyl)phenyl]carbamoyl}amino)-3-fluorophenoxy]-N-methylpyridine-2-carboxamide Following the same procedure described in Example 1, the title compound was prepared from 2-chloro-3-(pentafluoro-λ$^6$-sulfanyl)aniline and 4-(4-amino-3-fluorophenoxy)-N-methylpyridine-2-carboxamide as a beige solid.

¹H NMR (400 MHz, DMSO-d$_6$): δ 9.53 (s, 1H), 9.11 (s, 1H), 8.85 (d, 1H), 8.80 (m, 1H), 8.52 (d, 1H), 8.37 (d, 1H), 8.23 (t, 1H), 7.30 (d, 1H), 7.10 (t, 1H), 7.42 (s, 1H), 7.37 (dd, 1H), 7.20 (dd, 1H), 7.10 (d, 1H), 2.80 (d, 3H).

Example 9

N-methyl-4-[4-({[4-(pentafluoro-λ$^6$-sulfanyl)phenyl]carbamoyl}amino)phenoxy]pyridine-2-carboxamide Following the same procedure described in Example 1, the title compound was prepared from 4-(pentafluoro-λ$^6$-sulfanyl)aniline and 4-(4-aminophenoxy)-N-methylpicolinamide as a white solid.

¹H NMR (400 MHz, acetone-d$_6$): δ 8.70 (s, 1H), 8.45 (d, 2H), 8.30 (bs, 1H), 7.80 (d, 2H), 7.75 (d, 2H), 7.70 (d, 2H), 7.55 (s, 1H), 7.18 (d, 2H), 7.06 (m, 1H), 2.53 (s, 3H).

Example 10

4-[3-fluoro-4-({[4-(pentafluoro-λ$^6$-sulfanyl)phenyl]carbamoyl}amino)phenoxy]-N-methylpyridine-2-carboxamide Following the same procedure described in Example 1, the title compound was prepared from 4-(pentafluoro-λ$^6$-sulfanyl)aniline and 4-(4-amino-3-fluorophenoxy)-N-methylpyridine-2-carboxamide as a white solid.

¹H NMR (400 MHz, DMSO-d$_6$): δ 9.57 (s, 1H), 8.80 (m, 1H), 8.75 (s, 1H), 8.53 (d, 1H), 8.20 (t, 1H), 7.82 (d, 2H), 7.75 (d, 2H), 7.42 (d, 1H), 7.35 (dd, 1H), 7.20 (dd, 1H), 7.08 (dd, 1H), 2.80 (d, 3H).

Example 11

4-[4-({[4-bromo-3-(pentafluoro-λ$^6$-sulfanyl)phenyl]carbamoyl}amino)phenoxy]-N-methylpyridine-2-carboxamide Step 1. 4-bromo-3-(pentafluoro-λ$^6$-sulfanyl)aniline To a solution of 3-(pentafluoro-λ$^6$-sulfanyl)aniline (13.46 g, 61.4 mmol) in DMF (123 ml) stirred in a 500 mL round-bottomed flask in an ice bath under a nitrogen atmosphere, NBS (12.02 g, 67.6 mmol) was added in one portion. The resulting mixture was stirred at room temperature for 4 hr. The reaction was worked up by the addition of H$_2$O and extracted with EtOAc (2×100 mL). The combined organic layer was washed with H$_2$O and brine. The organic layer was dried over MgSO$_4$, filtered and evaporated. The residue was purified by CombiFlash Rf system eluted with a gradient up to 20% EtOAC/hexanes of EtOAc on a 120 g column to afford the desired 4-bromo-3-(pentafluoro-λ$^6$-sulfanyl)aniline (11 g, 36.9 mmol, 60.1% yield).

¹H NMR (300 MHz, CDCl3): δ 7.47 (d, 1 H), 7.15 (d, 1 H), 6.64 (dd, 1 H), 3.91 (br S, 2 H).

Step 2. 1-bromo-4-isocyanato-2-(pentafluoro-λ⁶-sulfanyl)benzene

To a solution of 4-bromo-3-(pentafluoro-λ⁶-sulfanyl) aniline (2.36 g, 7.92 mmol, 1.0 eq) in toluene (70 mL) was added triphosgene (1.57 g, 5.3 mmol, 0.67 eq) under $N_2$ at room temperature. Triethylamine (1.31 mL, 9.37 mmol, 1.2 eq) was added dropwise by syringe. The mixture was stirred at 72° C. (oil bath) for 2 hrs. TLC (hexane/EtOAc=2/1, UV) indicated that starting material was consumed. The mixture was allowed to cool to room temperature. Hexane (100 mL) was added. The precipitate was removed by filtration, washed with hexane (30 mL). The combined filtrate was concentrated by evaporator in vacuo at 70° C. for 40 min to afford crude 1-bromo-4-isocyanato-2-(pentafluoro-λ⁶-sulfanyl)benzene as a brown liquid which was used immediately for the next reaction without further purification.

Step 3. 4-[4-({[4-bromo-3-(pentafluoro-λ⁶-sulfanyl) phenyl]carbamoyl}amino)phenoxy]-N-methylpyridine-2-carboxamide The crude 1-bromo-4-isocyanato-2-(pentafluoro-λ⁶-sulfanyl)benzene obtained above was dissolved in DCM (70 mL). 4-(4-aminophenoxy)-N-methylpicolinamide (1.54 g, 6.34 mmol, 0.8 eq) was added at room temperature under $N_2$. The mixture was stirred at room temperature for about 30 min, a lot of solid precipitated. DCM (30 mL) was added and made the mixture stirred at room temperature for 18 hrs. The solid was filtrated, washed with DCM (50 mL), dried under high vacuum to afford 2.6 g (yield 72%) of the title compound as a white solid.

$^1$H NMR (300 MHz, DMSO-d6): δ 9.30 (s, 1 H), 9.03 (s, 1 H), 8.78 (d, 1 H), 8.50 (d, 1 H), 8.39 (s, 1 H), 7.81 (d, 1 H), 7.56 (m, 3 H), 7.38 (d, 1 H), 7.16 (m, 3 H), 2.78 (d, 3 H).

Example 12

4-[4-({[4-bromo-3-(pentafluoro-λ⁶-sulfanyl)phenyl]carbamoyl}amino)phenoxy]-N-methylpyridine-2-carboxamide, p-toluenesulfonate 4-[4-({[4-bromo-3-(pentafluoro-λ⁶-sulfanyl)phenyl]carbamoyl}amino)phenoxy]-N-methylpyridine-2-carboxamide (2.5 g, 4.4 mmol, 1.0 eq) was suspended in EtOH (dry, 45 mL). It was heated by a heat-gun until a clear solution formed. 4-methylbunzenefulfonic acid acid monohydrate (1.0 g, 5.29 mmol, 1.2 eq) was added in one portion. The solution was allowed to cool to room temperature. Solid was precipitated. The mixture was stirred at room temperature for 1.0 h, and then concentrated in vacuo to give the residue. EtOAc (60 mL) was added. The mixture was refluxed for 16 hrs, allowed to cool to room temperature. The solid was collected by filtration, washed with EtOAc (30 mL), then dried under high vacuum to afford 3.24 g of the title compound as a white solid.

$^1$H NMR (300 MHz, DMSO-d$_6$): δ 9.43 (s, 1 H), 9.17 (s, 1 H), 8.91 (m, 1 H), 8.54 (d, 1 H), 8.41 (s, 1 H), 7.83 (s, 1 H), 7.80 (s, 1 H), 7.63 (s, 1 H), 7.60 (s, 1 H), 7.52 (m, 4 H), 7.17 (m, 5 H), 2.80 (d, 3 H), 2.29 (s, 3 H).

Example 13

4-[4-({[4-bromo-3-(pentafluoro-λ⁶-sulfanyl)phenyl]carbamoyl}amino)-3-fluorophenoxy]-N-methylpyridine-2-carboxamide The crude 1-bromo-4-isocyanato-2-(pentafluoro-λ⁶-sulfanyl)benzene was dissolved in DCM (70 mL). 4-(4-amino-3-fluorophenoxy)-N-methylpicolinamide (1.75 g, 6.71 mmol, 0.8 eq) was added at room temperature under $N_2$. The mixture was stirred at room temperature for about 30 min, a lot of solid precipitated. DCM (30 mL) was added and made the mixture stirred at room temperature for 18 hrs. The solid was collected by filtration, washed with DCM (50 mL), and dried under high vacuum to afford 2.9 g of the title compound as a white solid.

$^1$H NMR (300 MHz, DMSO-d$_6$): δ 9.59 (s, 1 H), 8.77 (m, 2 H), 8.52 (d, 1 H), 8.41 (s, 1 H), 8.13 (m, 1 H), 7.82 (d, 1 H), 7.47 (m, 1 H), 7.42 (s, 1 H), 7.34 (m, 1 H), 7.19 (m, 1 H), 7.07 (m, 1 H), 2.79 (d, 3 H).

Example 14

4-[4-({[4-bromo-3-(pentafluoro-λ⁶-sulfanyl)phenyl]carbamoyl}amino)-3-fluorophenoxy]-N-methylpyridine-2-carboxamide, p-toluenesulfonate 4-[4-({[4-bromo-3-(pentafluoro-λ⁶-sulfanyl)phenyl]carbamoyl}amino)-3-fluorophenoxy]-N-methylpyridine-2-carboxamide (2, 0.86 mmol, 1.0 eq) was suspended in EtOH (dry, 10 mL). It was heated by a heat-gun until the clear solution formed. 4-methylbunzenefulfonic acid monohydrate (197 mg, 1.03 mmol, 1.2 eq) was added in one portion. The solution was allowed to cool to room temperature and stirred at room temperature for 1.0 h, then concentrated in vacuo to give the residue. EtOAc (15 mL) was added. The mixture was refluxed for 16 hrs, allowed to cool to room temperature. The solid was collected by filtration, washed with EtOAc (10 mL), then dried under high vacuum to afford 645 mg of the title compound as a white solid.

$^1$H NMR (300 MHz, DMSO-d$_6$): δ 9.64 (s, 1 H), 8.91 (m, 1 H), 8.81 (s, 1 H), 8.57 (d, 1 H), 8.43 (d, 1 H), 8.14 (t, 1 H), 7.82 (d, 1 H), 7.50 (m, 4 H), 7.36 (dd, 1 H), 7.26 (dd, 1 H), 7.11 (m, 3 H), 2.81 (d, 3 H), 2.29 (s, 3 H).

Example 15

4-[4-({[4-chloro-3-(pentafluoro-λ⁶-sulfanyl)phenyl]carbamoyl}amino)phenoxy]-N-methylpyridine-2-carboxamide, p-toluenesulfonate 4-[4-({[4-chloro-3-(pentafluoro-λ⁶-sulfanyl)phenyl]carbamoyl}amino)phenoxy]-N-methylpyridine-2-carboxamide (2.0 g, 3.82 mmol, 1.0 eq) was suspended in EtOH (dry, 45 mL). It was heated by a heat-gun until a clear solution formed. 4-methylbunzenefulfonic acid monohydrate (1.0 g, 5.29 mmol, 1.2 eq) was added in one portion. The solution was allowed to cool to room temperature and stirred at room temperature for 1 h, then concentrated in vacuo to give the residue. EtOAc (60 mL) was added. The mixture was refluxed for 16 hrs, allowed to cool to room temperature. The solid was collected by filtration, washed with EtOAc (30 mL), then dried under high vacuum to afford 2.65 g of the title compound as a white solid.

$^1$H NMR (300 MHz, DMSO-d$_6$): δ 9.43 (s, 1 H), 9.18 (s, 1 H), 8.93 (m, 1 H), 8.54 (d, 1 H), 8.42 (s, 1 H), 7.62 (m, 4 H), 7.51 (m, 3 H), 7.18 (m, 5 H), 2.80 (d, 3 H), 2.29 (s, 3 H).

Example 16

4-[4-({[4-chloro-3-(pentafluoro-λ⁶-sulfanyl)phenyl]carbamoyl}amino)-3-fluorophenoxy]-N-methylpyridine-2-carboxamide, p-toluenesulfonate 4-[4-({[4-chloro-3-(pentafluoro-λ⁶-sulfanyl)phenyl]carbamoyl}amino)-3-fluorophenoxy]-N-methylpyridine-2-carboxamide (2.06 g, 3.8 mmol, 1.0 eq) was suspended in EtOH (dry, 45 mL). It was heated by a heat-gun until a clear solution formed. 4-methylbunzenefulfonic acid monohydrate (868 mg, 4.56 mmol, 1.2 eq) was added in one portion. The solution was allowed to cool to room temperature and stirred at room temperature for 1 h, then concentrated in vacuo to give a white solid. EtOAc (60 mL) was added. The mixture was refluxed for 16 hrs, allowed to cool to room temperature. The solid was collected by filtration, washed with EtOAc (30 mL), then dried under high vacuum to afford 2.66 g of the title compound as a white solid.

$^1$H NMR (300 MHz, DMSO-$d_6$): δ 9.63 (s, 1 H), 8.88 (m, 1 H), 8.79 (m, 1 H), 8.55 (d, 1 H), 8.43 (d, 1 H), 8.14 (t, 1 H), 7.62 (m, 2 H), 7.48 (m, 3 H), 7.36 (dd, 1 H), 7.24 (dd, 1 H), 7.10 (m, 3 H), 2.80 (d, 3 H), 2.29 (s, 3 H).

Example 17

4-[4-({[2-chloro-5-(pentafluoro-$\lambda^6$-sulfanyl)phenyl] carbamoyl}amino)phenoxy]-N-methylpyridine-2-carboxamide, p-toluenesulfonate 4-[4-({[2-chloro-5-(pentafluoro-$\lambda^6$-sulfanyl)phenyl] carbamoyl}amino)phenoxy]-N-methylpyridine-2-carboxamide (1.7 g, 3.25 mmol, 1.0 eq) was suspended in EtOH (dry, 50 mL). It was heated by a heat-gun until a clear solution formed. 4-methylbunzenefulfonic acid monohydrate (742 mg, 3.9 mmol, 1.2 eq) was added in one portion. The solution was allowed to cool to room temperature and stirred at room temperature for 1 h, then concentrated in vacuo to give white solid. EtOAc (50 mL) was added. The mixture was refluxed for 16 hrs, allowed to cool to room temperature. The solid was collected by filtration, washed with EtOAc (25 mL), then dried under high vacuum to afford 2.13 g of the title compound as a white solid.

$^1$H NMR (300 MHz, DMSO-$d_6$): δ 9.76 (s, 1 H), 8.92 (m, 1 H), 8.85 (d, 1 H), 8.72 (s, 1 H), 8.55 (d, 1 H), 7.73 (m, 1 H), 7.55 (m, 6 H), 7.23 (m, 3 H), 7.13 (s, 1 H), 7.10 (s, 1 H), 2.80 (d, 3 H), 2.28 (s, 3 H).

Biological Test 1. In Vitro Kinase Assay for BRAF, FLT3 and KDR(VEGFR2)

The inhibitory activities of the compounds of the invention were measured by Invitrogen's SelectScreen® Profiling Service. The percentage of inhibition at concentration of 0.1 μM is summarized in Table 1.

TABLE 1

| Compound No. | [c], μM | Kinase | Inhibition |
|---|---|---|---|
| Example 1 | 0.1 | BRAF | 18% |
|  |  | FLT3 | 85% |
|  |  | KDR | 79% |
| Example 2 | 0.1 | BRAF | 14% |
|  |  | FLT3 | 71% |
|  |  | KDR | 76% |
| Example 3 | 0.1 | BRAF | 11% |
|  |  | FLT3 | 72% |
|  |  | KDR | 64% |
| Example 4 | 0.1 | BRAF | 8% |
|  |  | FLT3 | 51% |
|  |  | KDR | 36% |

Biological Test 2. Cell Death Detection Using Trypan Blue Exclusion Assay.

After drug treatment, cells were harvested by trypsinization with trypsin/EDTA for 10 min at 37° C. As some apoptotic cells detached from the culture substratum into the medium, these cells were also collected by centrifugation of the medium at 1,200 rpm for 5 min. The pooled cell pellets were resuspended and mixed with trypan blue dye. After Trypan blue stain was done, cells were counted by using a light microscope and a hemocytometer. Blue dye-incorporating cells were scored as being dead. Five hundred cells from randomly chosen fields were counted, and the number of dead cells was counted and expressed as a percentage of the total number of cells counted as shown in Tables 2 to 8 below.

TABLE 2

Hep3B (human human hepatoma cell line), 5-day treatment

| | Cell Death (%) at Tested Concentration | | | |
|---|---|---|---|---|
| Compound No. | 0 | 0.25 uM | 3.0 uM | 5.0 uM |
| Example 1 | 3.6 | 3.8 | 22.3 | 92.7 |
| Example 2 | 3.6 | 4.1 | 92.7 | 98.5 |
| Example 3 | 3.6 | 3.3 | 25.6 | 90.7 |
| Example 4 | 3.6 | 4.6 | 67.2 | 96.7 |
| Example 6 | 3.6 | 3.9 | 38.4 | 89.6 |
| Example 10 | 3.6 | 3.4 | 7.6 | 19.5 |
| Sorafenib | 3.6 | 3.0 | 12.5 | 88.2 |

TABLE 3

HepG2 (human human Hepatocellular carcinoma cell line), 5-day treatment

| | Cell Death (%) at Tested Concentration | | | |
|---|---|---|---|---|
| Compound No. | 0 | 0.25 uM | 3.0 uM | 5.0 uM |
| Example 1 | 2.3 | 2.6 | 32.4 | 84.5 |
| Example 2 | 2.3 | 2.2 | 94.7 | 99 |
| Example 3 | 2.3 | 2.7 | 4.2 | 14.6 |
| Example 4 | 2.3 | 1.9 | 4.5 | 27.6 |
| Example 6 | 2.3 | 2.6 | 90.7 | 99 |
| Example 10 | 2.3 | 2.7 | 4.2 | 4.8 |
| Sorafenib | 2.3 | 2.2 | 6.4 | 8.2 |

TABLE 4

HT29 (human colon adenocarcinoma cell line), 5-day treatment

| | Cell Death (%) at Tested Concentration | | | |
|---|---|---|---|---|
| Compound No. | 0 | 2.5 uM | 5.0 uM | 10 uM |
| Example 1 | 11.2 | 12.4 | 14.5 | 68.7 |
| Example 2 | 11.2 | 12.3 | 14.7 | 24.8 |
| Example 3 | 11.2 | 11.4 | 16.7 | 30.7 |
| Example 4 | 11.2 | 11.6 | 13.8 | 44.6 |
| Example 6 | 11.2 | 11.7 | 13.4 | 22.1 |
| Example 10 | 11.2 | 18.3 | 54.6 | 56.7 |
| Sorafenib | 11.2 | 11.6 | 14.3 | 27.6 |

TABLE 5

HUH7 (human hepatoma cell line), 7-day treatment

| | Cell Death (%) at Tested Concentration | | | | | |
|---|---|---|---|---|---|---|
| Compound No. | 0 | 1.0 uM | 2.5 uM | 5.0 uM | 7.5 uM | 10 uM |
| Example 1 | 2.2 | 2.0 | 5.1 | 18.3 | 52.7 | 72.3 |
| Example 2 | 2.2 | 2.4 | 7.3 | 42.6 | 72.6 | 75.2 |
| Example 3 | 2.2 | 2.7 | 4.5 | 53.8 | 79.6 | 87.6 |
| Example 4 | 2.2 | 2.8 | 3.1 | 59.8 | 91.4 | 93.4 |
| Example 5 | 2.2 | 1.7 | 3.1 | 4.3 | 17.2 | 19.8 |
| Example 6 | 2.2 | 2.0 | 2.2 | 7.4 | 32.1 | 35.4 |
| Example 10 | 2.2 | 1.9 | 2.2 | 17.2 | 87.6 | 93.7 |
| Sorafenib | 2.2 | 2.4 | 2.1 | 16.3 | 76.8 | 90.4 |

TABLE 6

LNCaP (human prostate adenocarcinoma cell line), 3-day treatment

| | Cell Death (%) at Tested Concentration | | | | |
|---|---|---|---|---|---|
| Compound No. | 0 | 1.0 uM | 2.5 uM | 5.0 uM | 7.5 uM | 10 uM |
| Example 1 | 1.2 | 1.6 | 1.5 | 1.3 | 7.3 | 62.5 |
| Example 2 | 1.2 | 1.7 | 1.8 | 1.6 | 4.2 | 83.7 |
| Example 3 | 1.2 | 1.3 | 1.9 | 4.3 | 13.4 | 91.8 |
| Example 4 | 1.2 | 1.8 | 1.4 | 2.8 | 46.8 | 94.8 |
| Example 5 | 1.2 | 1.0 | 1.5 | 1.4 | 2.1 | 7.6 |
| Example 6 | 1.2 | 1.1 | 1.3 | 1.2 | 3.6 | 4.3 |
| Example 10 | 1.2 | 1.8 | 1.9 | 9.4 | 11.3 | 68.3 |
| Sorafenib | 1.2 | 1.6 | 1.7 | 2.3 | 2.4 | 81.3 |

TABLE 7

LNCaP (human prostate adenocarcinoma cell line), 7-day treatment

| | Cell Death (%) at Tested Concentration | | | | |
|---|---|---|---|---|---|
| Compound No. | 0 | 1.0 uM | 2.5 uM | 5.0 uM | 7.5 uM | 10 uM |
| Example 1 | 1.7 | 1.6 | 2.8 | 2.8 | 99 | 99 |
| Example 2 | 1.7 | 1.5 | 2.7 | 2.5 | 17.3 | 99 |
| Example 3 | 1.7 | 2.3 | 2.8 | 99 | 99 | 99 |
| Example 4 | 1.7 | 1.4 | 2.7 | 69.4 | 99 | 99 |
| Example 5 | 1.7 | 1.8 | 1.9 | 2.3 | 4.6 | 14.7 |
| Example 6 | 1.7 | 1.7 | 1.9 | 2.4 | 4.8 | 13.4 |
| Example 10 | 1.7 | 2.2 | 2.8 | 99 | 99 | 99 |
| Sorafenib | 1.7 | 1.6 | 1.6 | 2.8 | 14.7 | 99 |

TABLE 8

HUH7 (human hepatoma cell line), 6-day treatment in combination with AZD-6244 (MEK inhibitor)

| | Cell Death (%) in combination with AZD-6244 AZD-6244 Concentration | |
|---|---|---|
| Compound | 0 μM | 0.5 μM |
| 0 | 1.6 | 2.3 |
| Example 1, 0.5 μM | 2.3 | 99 |
| Example 2, 0.5 μM | 3.6 | 99 |
| Example 3, 0.5 μM | 1.9 | 94.6 |
| Example 4, 0.5 μM | 2.6 | 99 |
| Example 6, 0.5 μM | 2.1 | 99 |
| Example 10, 0.5 μM | 1.7 | 94.6 |
| Sorafenib, 0.5 μM | 1.9 | 97.3 |

Biological Test 3. In Vivo Toxicity Study in Mice

A 24-day treatment of mice with compounds of this invention and comparables (Sorefenib and Regorafenib) was conducted to determine the in vivo toxicity of the compounds of this invention. Each compound was administered to the mice on a 20-25 mg/kg/day regime for 24 consecutive days. While the mice administered with Sorefenib or Regorafenib had a 60-66% death rate following the study, the tested compounds of this invention show either comparable or much lower toxicity in the test, showing 0% to 70% of death rate.

Biological Test 4. In Vivo Activity in Senograph SCID Mouse Model with Lung Cancer A 30-day treatment of patient-derived primary squamous lung 14531 tumor in mouse was conducted with Examples 4 and 10 of this invention and with Sorafenib. Compared to the control, all three compounds showed significant effect in reducing the tumor volume in their respective animal group. The tested compounds of this invention in generally showed even more superior efficacy in reducing the tumor volumes in the mice.

Biological Test 5. In Vivo Activity in Senograph SCID Mouse Model with Lung Cancer A 30-day treatment of patient-derived primary squamous lung 14531 tumor in mouse was conducted with Examples 4 and 10 of this invention and with Sorafenib. Compared to the control, all three compounds showed significant effect in reducing the tumor volume in their respective animal groups. The tested compounds of this invention generally showed even more superior efficacy in reducing the tumor volumes in the mice.

Other Embodiments

It is to be understood that while the invention has been described in conjunction with the detailed description thereof, the foregoing description is intended to illustrate and not limit the scope of the invention, which is defined by the scope of the following claims. Other aspects, advantages, and modifications are within the scope of the following claims. All publications referenced herein are incorporated by reference in their entireties.

What is claimed is:

1. A compound of Formula (I) or a pharmaceutically acceptable salt, metabolite, or isolated stereoisomer thereof,

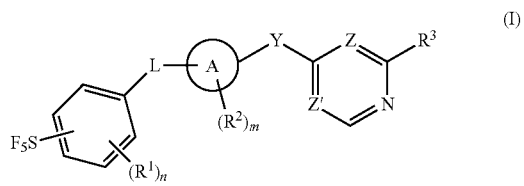

wherein:
Y is O, S, S(O), S(O)$_2$, or NR$^4$;
L is —NR$^4$—X—, —X—NR$^4$—, —NR$^4$—X—NR$^4$—, —NR$^4$—, O, S;
X is —C(O)—, —C(S)—, —S(O)$_2$—, or

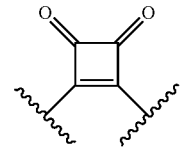 [SMILES: *c1c(*)c(=O)c1=O]

Z and Z' are each CH;
R$^1$ and R$^2$ are each independently alkyl, substituted alkyl, alkoxy, substituted alkoxy, amino, substituted amino, or halo;
R$^3$ is hydrogen, halo, alkyl, substituted alkyl, alkenyl, substituted alkenyl, alkynyl, substituted alkynyl, carbonitrile, aryl, substituted aryl, cycloalkyl, substituted cycloalkyl, cycloalkenyl, substituted cycloalkenyl, heteroaryl, substituted heteroaryl, heterocyclyl, substituted heterocyclyl, amino, substituted amino, acyl, acylamino, alkoxy, substituted alkoxy, carboxyl, carboxyl ester, substituted C$_{1-6}$alkylsulfonyl, aminosulfonyl, or aminocarbonyl;
each R$^4$ is independently hydrogen or alkyl;
Ring A is aryl or heteroaryl; and
m and n are each independently 0, 1, 2, or 3.

2. The compound of claim 1, wherein Y is O, S, or NR$^4$.

3. The compound of claim 2, wherein Y is O or S.

4. The compound of claim 1, wherein Ring A is phenyl.

5. The compound of claim 1, wherein $R^1$ and $R^2$ are each independently alkyl or halo.

6. The compound of claim 5, wherein $R^1$ and $R^2$ are each independently halo.

7. The compound of claim 6, wherein $R^1$ and $R^2$ are each independently F, Cl, or Br.

8. The compound of claim 1, wherein $R^3$ is hydrogen, halo, carboxyl, carboxyl ester, or aminocarbonyl.

9. The compound of claim 8, wherein $R^3$ is aminocarbonyl.

10. The compound of claim 9, wherein $R^3$ is methylaminocarbonyl.

11. The compound of claim 1, wherein m and n are each independently 0 or 1.

12. The compound of claim 1, wherein the compound is of Formula (II), and Y and W are each independently O or S,

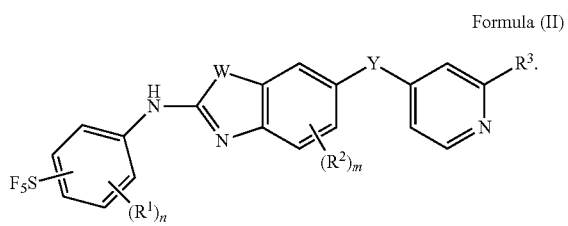

Formula (II)

13. The compound of claim 12, wherein the compound is of Formula (III); $R^1$ and $R^2$ are each independently halo; and $R^5$ is hydrogen or substituted alkyl,

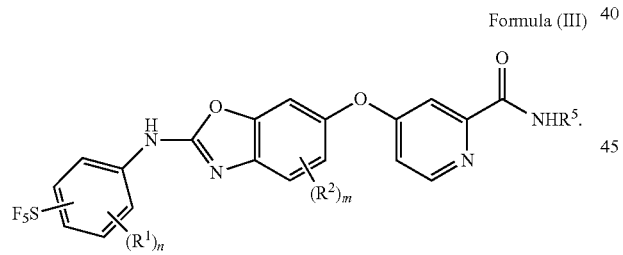

Formula (III)

14. The compound of claim 1, wherein the compound is of Formula (IV), and Y is O or S,

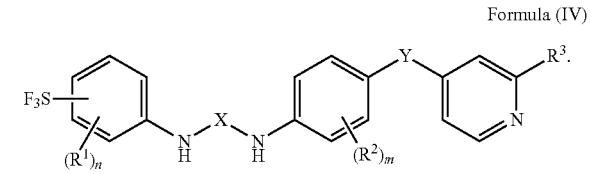

Formula (IV)

15. The compound of claim 14, wherein the compound is of Formula (V), $R^1$ and $R^2$ are each independently hydrogen or halo, and $R^5$ is hydrogen, alkyl, or substituted alkyl,

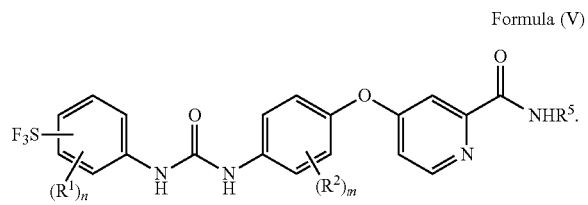

Formula (V)

16. The compound of claim 1, wherein the compound is:
N-Methyl-4-[4-({[3-(pentafluoro-λ⁶-sulfanyl)phenyl]carbamoyl}amino)phenoxy]-pyridine-2-carboxamide;
4-[3-Fluoro-4-({[3-(pentafluoro-λ⁶-sulfanyl)phenyl]carbamoyl}amino)phenoxy]-N-methylpyridine-2-carboxamide;
4-[4-({[4-Chloro-3-(pentafluoro-λ⁶-sulfanyl)phenyl]carbamoyl}amino)phenoxy]-N-methylpyridine-2-carboxamide;
4-[4-({[4-Chloro-3-(pentafluoro-λ⁶-sulfanyl)phenyl]carbamoyl}amino)-3-fluorophenoxy]-N-methylpyridine-2-carboxamide;
4-[4-({[2-Chloro-5-(pentafluoro-λ⁶-sulfanyl)phenyl]carbamoyl}amino)phenoxy]-N-methylpyridine-2-carboxamide;
4-[4-({[2-Chloro-5-(pentafluoro-λ⁶-sulfanyl)phenyl]carbamoyl}amino)-3-fluorophenoxy]-N-methylpyridine-2-carboxamide;
4-[4-({[2-Chloro-3-(pentafluoro-λ⁶-sulfanyl)phenyl]carbamoyl}amino)phenoxy]-N-methylpyridine-2-carboxamide;
4-[4-({[2-Chloro-3-(pentafluoro-λ⁶-sulfanyl)phenyl]carbamoyl}amino)-3-fluorophenoxy]-N-methylpyridine-2-carboxamide;
N-Methyl-4-[4-({[4-(pentafluoro-λ⁶sulfanyl)phenyl]carbamoyl}amino)phenoxy]-pyridine-2-carboxamide;
4-[3-Fluoro-4-({[4-(pentafluoro-λ⁶-sulfanyl)phenyl]carbamoyl}amino)phenoxy]-N-methylpyridine-2-carboxamide;
4-[4-({[4-bromo-3-(pentafluoro-λ⁶-sulfanyl)phenyl]carbamoyl}amino)phenoxy]-N-methylpyridine-2-carboxamide;
4-[4-({[4-bromo-3-(pentafluoro-λ⁶-sulfanyl)phenyl]carbamoyl}amino)phenoxy]-N-methylpyridine-2-carboxamide, p-toluenesulfonate;
4-[4-({[4-bromo-3-(pentafluoro-λ⁶-sulfanyl)phenyl]carbamoyl}amino)-3-fluorophenoxy]-N-methylpyridine-2-carboxamide;
4-[4-({[4-bromo-3-(pentafluoro-λ⁶-sulfanyl)phenyl]carbamoyl}amino)-3-fluorophenoxy]-N-methylpyridine-2-carboxamide, p-toluenesulfonate;
4-[4-({[4-chloro-3-(pentafluoro-λ⁶-sulfanyl)phenyl]carbamoyl}amino)phenoxy]-N-methylpyridine-2-carboxamide, p-toluenesulfonate;
4-[4-({[4-chloro-3-(pentafluoro-λ⁶-sulfanyl)phenyl]carbamoyl}amino)-3-fluorophenoxy]-N-methylpyridine-2-carboxamide, p-toluenesulfonate; or
4-[4-({[2-chloro-5-(pentafluoro-λ⁶-sulfanyl)phenyl]carbamoyl}amino)phenoxy]-N-methylpyridine-2-carboxamide, p-toluenesulfonate.

17. The compound of claim 1, wherein the compound is a pharmaceutically acceptable salt of hydrochloric acid, hydrobromic acid, sulfuric acid, phosphoric acid, methanesulfonic acid, trifluoromethanesulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, or mandelic acid.

18. A pharmaceutical composition comprising a compound of claim 1 and a physiologically acceptable carrier.

19. A method for treating a disease in a mammal that is mediated by protein kinase, comprising administering to the mammal in need thereof a therapeutically effective amount of a compound of claim 1 wherein the disease is lung cancer, liver cancer, colon cancer, or prostate cancer.

20. The method of claim 19, wherein the protein kinase is VEGFR-2, PDGFR, raf kinase, or FLT3, or c-Kit.

21. The method of claim 19, further comprising administering to the mammal an additional anti-cancer agent.

* * * * *